(12) United States Patent
Wayne et al.

(10) Patent No.: US 10,598,592 B1
(45) Date of Patent: Mar. 24, 2020

(54) RETROREFLECTIVE OPTICAL SYSTEM AND METHODS

(71) Applicant: SPAWAR Systems Center Pacific, San Diego, CA (US)

(72) Inventors: David T. Wayne, San Diego, CA (US); Burton H. Neuner, III, San Diego, CA (US)

(73) Assignee: UNITED STATES OF AMERICA AS REPRESENTED BY THE SECRETARY OF THE NAVY, Washington, DC (US)

( * ) Notice: Subject to any disclaimer, the term of this patent is extended or adjusted under 35 U.S.C. 154(b) by 0 days.

(21) Appl. No.: 16/280,954

(22) Filed: Feb. 20, 2019

(51) Int. Cl.
| | |
|---|---|
| G01N 21/55 | (2014.01) |
| G02B 5/30 | (2006.01) |
| H04B 10/532 | (2013.01) |
| G01N 21/552 | (2014.01) |

(52) U.S. Cl.
CPC ........... G01N 21/55 (2013.01); G01N 21/552 (2013.01); G01N 21/553 (2013.01); G02B 5/30 (2013.01); H04B 10/532 (2013.01); G01N 2021/551 (2013.01); G01N 2021/557 (2013.01); G01N 2021/558 (2013.01)

(58) Field of Classification Search
CPC .................. G01N 21/00; G01N 21/55; G01N 21/552–21/554; G01N 21/63; G01N 21/6428; G01N 2021/551; G01N 2021/557; G01N 2021/558; G02B 5/30; H04B 10/532

USPC ............................ 356/139.03, 620, 622, 624
See application file for complete search history.

(56) References Cited

U.S. PATENT DOCUMENTS

| | | | |
|---|---|---|---|
| 6,810,141 B2 | 10/2004 | Barbour | |
| 7,703,931 B2* | 4/2010 | Nilsen | G02B 5/124 |
| | | | 359/530 |
| 9,612,370 B1* | 4/2017 | Johnson | G02B 19/0095 |
| 10,386,463 B1* | 8/2019 | Schubert | G01S 17/89 |
| 2005/0185283 A1* | 8/2005 | Belenkii | G02B 5/132 |
| | | | 359/627 |
| 2018/0197052 A1* | 7/2018 | Yanson | G06K 19/0614 |

OTHER PUBLICATIONS

Rosenkranz et al., "Electro-optic modulator based on a metel-ferroelectric nocomposite," Proceedings of SPIE, vol. 8809 (Sep. 11, 2013).

(Continued)

Primary Examiner — Colin W Kreutzer
(74) Attorney, Agent, or Firm — Naval Information Warfare Center, Pacific; Kyle Eppele; James R. McGee

(57) ABSTRACT

A retroreflective optical system for creating a passive optical tag in an absence of electrical power, involving: a retroreflector having a surface and a retroreflective element disposed in relation to the surface, the retroreflective element configured to: passively impart a unique signature in relation to incoming light by using at least one of spectral filtration and color filtration, whereby a plasmonic response is effectible; and reflect outgoing light having the unique signature; and an optical device having an input aperture, the optical device disposed at a distance from the retroreflector and configured to transmit the incoming light and the outgoing light.

20 Claims, 7 Drawing Sheets

(56) References Cited

OTHER PUBLICATIONS

Swedberg, Claire, "Kodak Markets Optical Marker as RFID Alternative," RFID Journal, Apr. 1, 2008, http://www.rfidjournal.com/articles/view?3995 (Aug. 1. 2008).

Imagineered Products and Services, "Optically Powered RFID Tags and Optical Tag Readers," Imagineering—eZine, Dec. 11, 2015, http://www.imagineeringezine.com/e-zine/OPID.html (Dec. 11, 2015).

Raether, H., "Surface Plasmons on Smooth and Rough Surfaces and on Gratings," Springer Tracts in Modern Physics, vol. 111; Springer-Verlag, Bedin; Germany (1988).

Lynch, David W. et al., "Handbook of Optical Constants of Solids," E. D. Palik, Ed., Academic Press, Orlando, FL, p. 294 (1985).

Alterovitz, Samuel A., et al., "Cubic Silicon Carbide . . . " in "Handbook of Optical Constants of Solids II," E.D., Palik, Ed., Academic Press, New York, NY, pp. 705-707 (1991).

* cited by examiner

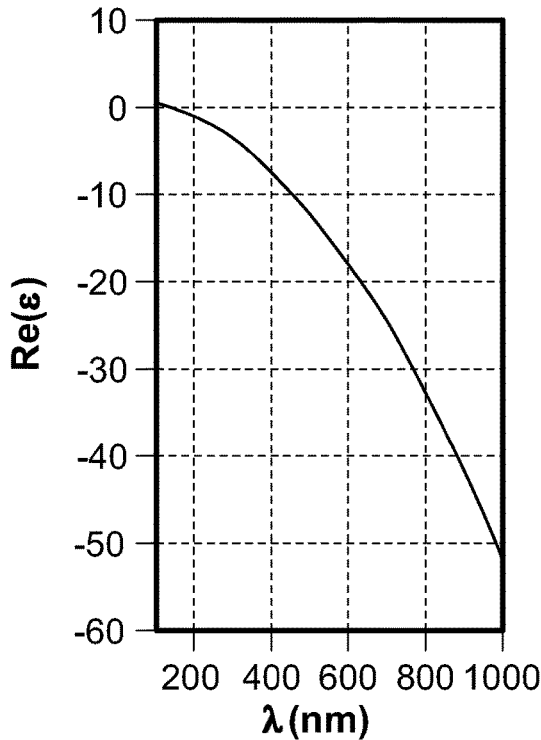
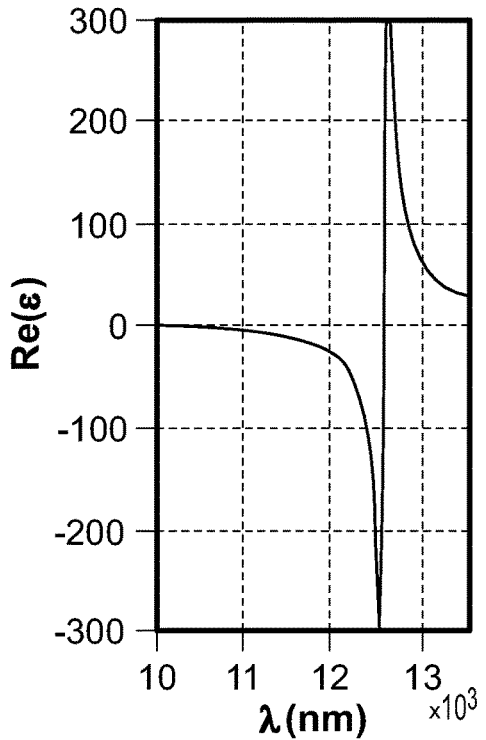
FIG. 1A
FIG. 1B
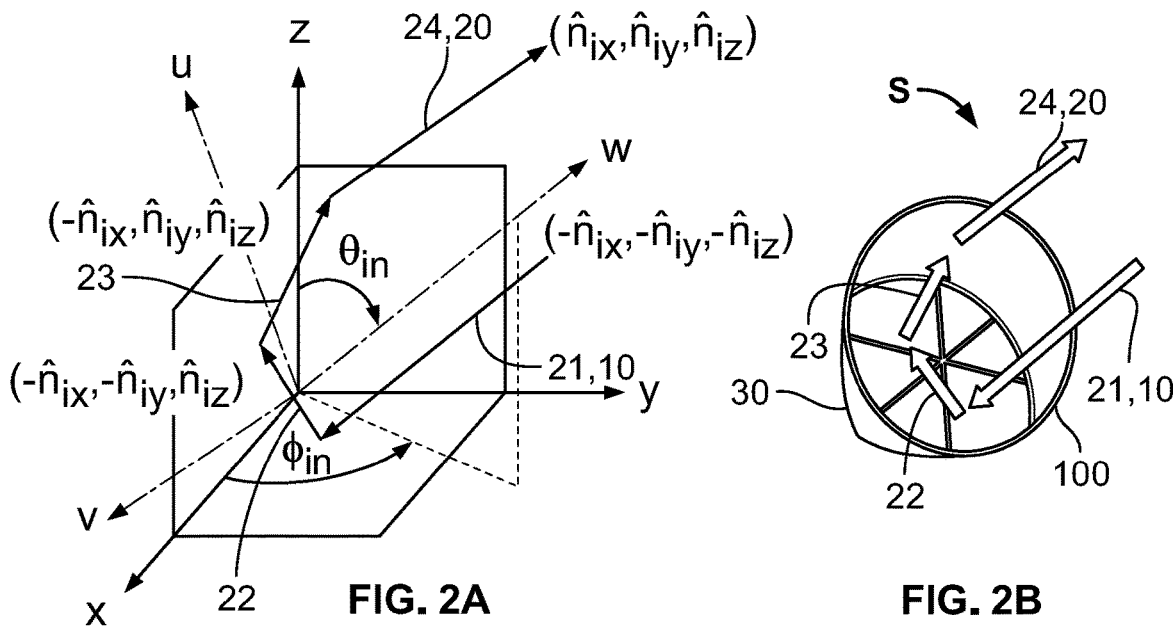
FIG. 2A
FIG. 2B

Unpolarized Product, $d_{Au}$=55nm, $n_{CCR}$=1.4, $n_{film}$=1.1, AZ=42.0°, EL=54.7°, $\theta_{normal}$=2.4°

Unpolarized Product, $d_{Au}$=55nm, $n_{CCR}$=1.4, $n_{film}$=1.1, AZ=44.0°, EL=54.7°, $\theta_{normal}$=0.8°

Unpolarized Product, $d_{Au}$=55nm, $n_{CCR}$=1.4, $n_{film}$=1.1, AZ=45.0°, EL=54.7°, $\theta_{normal}$=0.0°

Unpolarized Product: $d_{SiC}$=750nm, $n_{CCR}$=3.48, $n_{film}$=2, AZ=45.0°, EL=54.7°, $\theta_{normal}$=0.0°

Unpolarized Product: $d_{SiC}$=750nm, $n_{CCR}$=3.48, $n_{film}$=2, AZ=30.0°, EL=30.0°, $\theta_{normal}$=66.8°

Unpolarized Product: $d_{SiC}$=750nm, $n_{CCR}$=3.48, $n_{film}$=2, AZ=20.0°, EL=30.0°, $\theta_{normal}$=82.5°

```
                                                      ┌─ M1
    801 ┐
    ┌─────────────────────────────────────────────────┐
    │ providing a retroreflector, providing the retroreflector comprising │
    │   providing a surface and providing a retroreflective element      │
    │  disposed in relation to the surface, providing the retroreflective │
    │      element comprising configuring the retroreflective element to: │
    │   passively impart a unique signature in relation to incoming light │
    │      by using at least one of spectral filtration and color filtration, │
    │    whereby a plasmonic response is effectible; and reflect outgoing │
    │                  light having the unique signature                  │
    └─────────────────────────────────────────────────┘
                              │
                              ▼
    802 ┐
    ┌─────────────────────────────────────────────────┐
    │         providing an optical device, providing the optical device   │
    │       comprising providing an input aperture, providing the optical │
    │      device comprising disposing the optical device at a distance   │
    │        from the retroreflector and configuring the optical device   │
    │            to transmit the incoming light and the outgoing light    │
    └─────────────────────────────────────────────────┘
```

RETROREFLECTIVE OPTICAL SYSTEM AND METHODS

FEDERALLY-SPONSORED RESEARCH AND DEVELOPMENT

The United States Government has ownership rights in the subject matter of this invention. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil. Reference Navy Case No. 103532.

BACKGROUND OF THE INVENTION

Technical Field

The present disclosure relates to optical technologies. Particularly, the present disclosure relates to retroreflective optical technologies.

Description of the Related Art

In the related art, devices are used for tagging an object at a standoff distance and subsequently interrogating the object, e.g., at a future time, whereby tracking is achieved for proper identification. The tag placed on the object emits a unique code or signature, thereby allowing the object to be identified among other objects. These related art devices, used for object identification, typically operate in the radio-frequency (RF) spectrum or operate by using electrical power for actively generating a unique optical signature. These related art devices, operating in the RF spectrum, are vulnerable to jamming and spectrum allocation issues. Further, the related art devices, operating by using electrical power for actively generating the unique optical signature, experience restrictions on the object intended for tagging. Such related art devices, using electrical power for actively generating the unique optical signature, typically employ modules, wherein such modules require electrical power for actively modulating a light source with a unique code in order to generate a signal, wherein receivers decode the signal and match the code with the associated optical tag.

Thus, a need exists in the related art for improving the identification process of objects at a standoff distance and for improving the power requirements.

SUMMARY OF THE INVENTION

The present disclosure generally involves a retroreflective optical system for creating a passive optical tag in an absence of electrical power, comprising: a retroreflector having a surface and a retroreflective element disposed in relation to the surface, the retroreflective element configured to: passively impart a unique signature in relation to incoming light by using at least one of spectral filtration and color filtration, whereby a plasmonic response is effectible; and reflect outgoing light having the unique signature; and an optical device having an input aperture, the optical device disposed at a distance from the retroreflector and configured to transmit the incoming light and the outgoing light.

BRIEF DESCRIPTION OF THE DRAWINGS

The above, and other, aspects and features of several embodiments of the present disclosure will be more apparent from the following Detailed Description of the Invention as presented in conjunction with the following several figures of the Drawings.

FIG. 1A is a graph illustrating permittivity, or reflectance Re(ε), of a retroreflective element, comprising gold, as a function of wavelength in nanometers (nm), in accordance with an embodiment of the present disclosure.

FIG. 1B is a graph illustrating permittivity, or reflectance Re(ε), of a retroreflective element, comprising silicon carbide, as a function of wavelength in nanometers (nm), in accordance with an embodiment of the present disclosure.

FIG. 2A is a diagram illustrating, in a perspective view, a coordinate system with a representation of direction and orientation of both incoming light and outgoing light as effected using a retroreflective optical system, in accordance with an embodiment of the present disclosure.

FIG. 2B is a diagram illustrating, in a perspective view, a retroreflective optical system with a representation of direction and orientation of both incoming light and outgoing light, in accordance with an embodiment of the present disclosure.

FIG. 8 is a flow diagram illustrating a method of fabricating a retroreflective optical system for creating a passive optical tag in an absence of electrical power, in accordance with an embodiment of the present disclosure.

Figure 3:
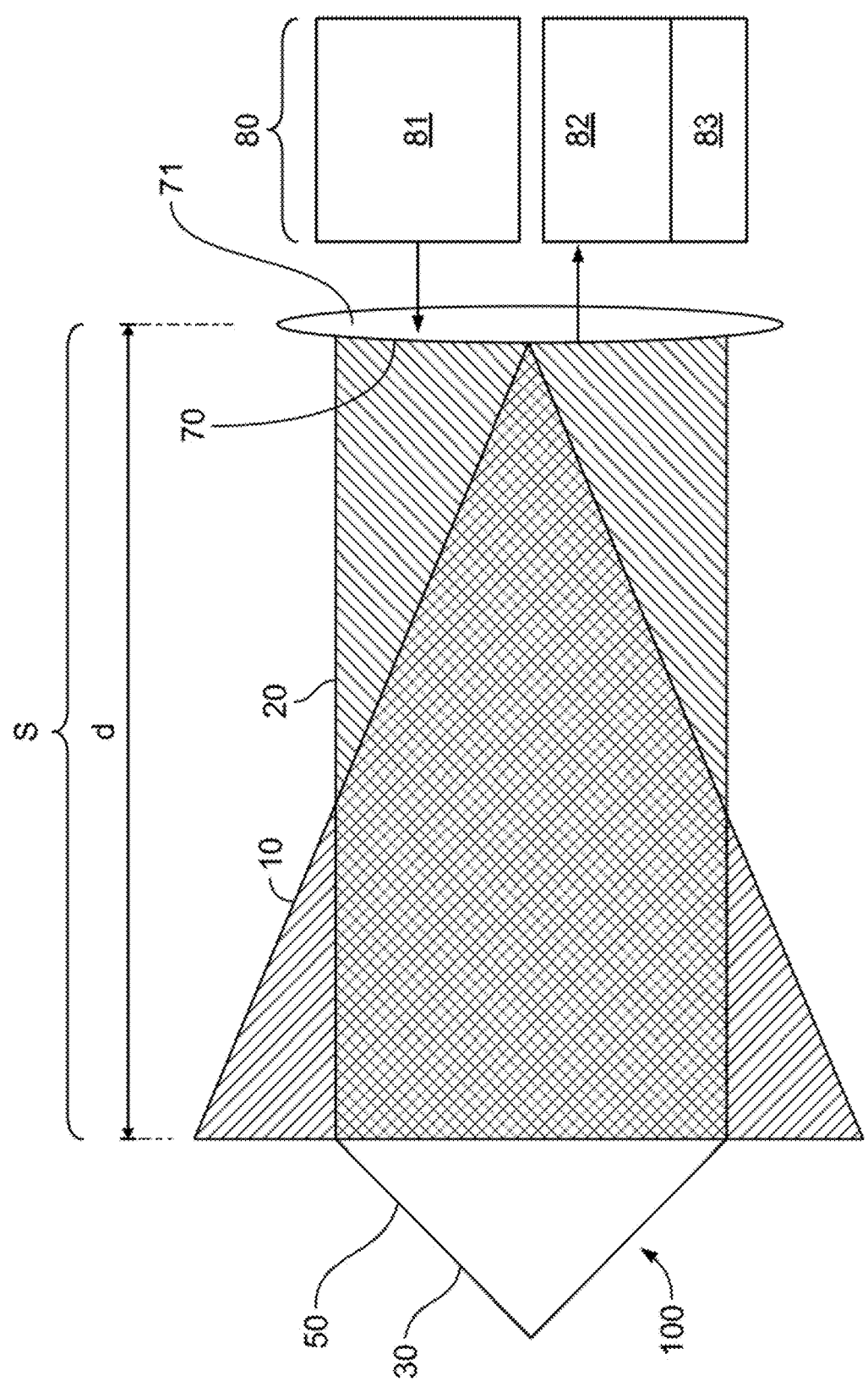
FIG. 3 is a diagram illustrating, in a side view, a retroreflective optical system as implemented with an optical source, e.g., a laser light source, in accordance with an embodiment of the present disclosure.

Corresponding reference numerals or characters indicate corresponding components throughout the several figures of the Drawings. Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood, elements that are useful or necessary in commercially feasible embodiments are often not depicted in order to facilitate a less obstructed view of these various embodiments of the present disclosure.

DETAILED DESCRIPTION OF THE INVENTION

In order to address many of the related art challenges, the present disclosure generally involves a retroreflective optical system for creating a passive optical tag in an absence of electrical power. The retroreflective optical system eliminates the related art need for using electrical power to generate a unique signature. The retroreflective element spectrally filters the reflected beam and, thus, reflects only selected light, wherein an object, bearing the retroreflective device, is uniquely distinguishable from other objects. Further, retroreflective element provides a spectral response; and this spectral response is usable for determining azimuth and elevation or orientation of the retroreflector.

In accordance with embodiments of the present disclosure, the retroreflective optical system utilizes plasmonic techniques. Surface plasmon-polaritons or surface phonon-polaritons (SPPs) are electromagnetic surface waves that are tightly confined to an interface between a polaritonic material (permittivity $\varepsilon<0$) and a dielectric material (permittivity $\varepsilon>0$). A negative permittivity arises from a collective oscillation of conduction electrons (plasmons) in metals, such as Au and silver (Ag), or from lattice vibrations (phonons) in polar crystals, such as SiC, zinc selenide (ZnSe), and indium phosphide (InP).

The surface plasmons are excitable by visible-range and near-infrared-range photons. Surface phonons occur in a mid-infrared range. In both of these modes, the nature of the excitation is such that the incident light source alone is insufficient to excite the mode, e.g., a longitudinal wavevector is insufficient to do so. For at least this reason, a coupling technique is implemented by the system and methods of the present disclosure.

The SPP propagation wavenumber $k_{SPP}$ (see also below Eq. 1) implies that $k_{SPP}>\omega/c$, wherein $\omega=2\pi c/\lambda$, wherein $\lambda$=the wavelength of light, and wherein c=the speed of light. Since the SPP wavenumber is larger than that provided by incident radiation, auxiliary coupling techniques, such as gratings and high-index prisms, are utilized by embodiments of the present disclosure for exciting surface waves. When a dielectric prism is used, either an Otto configuration or a Kretschmann configuration is employed. The Kretschmann configuration involves depositing a metal directly on a prism. In embodiments of the present disclosure, an evanescent electric field extends through the metal film and excites plasmons at an outer metal-air interface or a metal-film interface if protective film coatings are used.

The dielectric permittivity $\varepsilon$ indicates how a material responds to an incident electric field, e.g., matter, having $\varepsilon>0$, polarizes light in the same direction as the electric field vector E, whereas matter, having $\varepsilon<0$, polarizes light in the opposite direction as the electric field vector E. Metals and polar crystals exhibit negative permittivity in certain frequency ranges. For example, $\varepsilon<0$ occurs in metals for frequencies less than the plasma frequency and in polar crystals for frequencies between the transverse optical (TO) phonon mode and the longitudinal optical (LO) phonon mode (the Reststrahlen band). Free electron gas oscillation is responsible for the metal's plasmonic behavior. The coupling of photon radiation with a surface excitation is referred to as surface polariton generation.

The surface plasmon polariton, or surface phonon-polariton, dispersion relation is a unique excitation triggerable at the interface between materials having dielectric permittivity of opposite signs or polarities. While the physical mechanisms, behind $\varepsilon>0$, that are exhibited by metals differ from the physical mechanisms exhibited by crystals, their electromagnetic dispersion is the same, depending only on the frequency-dependent optical properties of each material.

The solutions of Maxwell's equations are classified into an s-polarized mode and a p-polarized mode, wherein the electric field E and the magnetic field H are respectively oriented parallel to the interface. Waves propagating along the interface comprise a component of electric field that is perpendicular to the surface. Thus, a p-polarization is used.

Referring to FIGS. 1A and 1B, together, the SPP wavevector dispersion relation is expressed in the following frequency-dependent equation:

$$k(\omega) = \frac{\omega}{c} \sqrt{\frac{\varepsilon_1 * \varepsilon_2(\omega)}{\varepsilon_1 + \varepsilon_2(\omega)}}, \tag{1}$$

wherein $\varepsilon_1$ corresponds to a dielectric layer, such as air or a protective film, and wherein $\varepsilon_2(\omega)$ corresponds to a frequency-dependent polaritonic material, such as a metal and a crystal. The permittivities of two materials, such as a metal, e.g., Au, and a polar crystalline material, e.g., SiC, are respectively shown in FIGS. 1A and 1B. Surface plasmon-polaritons in metals and surface phonon-polaritons in polar crystals are supported when the permittivity is less than zero.

Still referring to FIGS. 1A and 1B, together, FIG. 1A is a graph illustrating permittivity, or reflectance Re($\varepsilon$), of a retroreflective element comprising Au, e.g., metallic Au, as a function of wavelength in nanometers (nm); and FIG. 1B is a graph illustrating permittivity, or reflectance Re($\varepsilon$), of a retroreflective element comprising SiC, e.g., polar crystalline SiC, as a function of wavelength in nanometers (nm), in accordance with embodiments of the present disclosure. Mode excitation is effected by wavevector matching via external techniques, such as a prism and a grating. If using a prism, the dielectric prism dispersion is expressed by the following equation:

$$k_x = \frac{\omega}{c}\sqrt{\varepsilon_{CCR}}\sin\theta, \qquad (2)$$

wherein $k_x$=the prism dispersion line. Efficient coupling to SPPs through the prism, e.g., a corner cube retroreflector (CCR) occurs when $k_x$=Re ($k_{SPP}$) and is calculable by setting Eq. 1 equal to Eq. 2 (equality relationship). The CCR dielectric permittivity=$\varepsilon_{CCR}$ which is related to the index of refraction by $\varepsilon_{CCR}$=$\varepsilon_{CCR}^2$; and the incidence angle inside the prism=a generalized $\theta$.

Still referring to FIGS. 1A and 1B, together, when conditions are non-resonant, e.g., wavevectors are unmatched, the total internal reflection dominates; and near-unity light reflectivity is observed. However, for specific wavelengths and incident angles, that satisfy the foregoing equality relationship, an efficient polariton coupling occurs and is characterized by near-zero light reflectivity, whereby attenuated total reflection is providable and implemented by the embodiments of the present disclosure.

Referring to FIG. 2A, this diagram illustrates a perspective view of a coordinate system with a representation of direction and orientation of both incoming light 10 and outgoing light 20, as effected using a retroreflective optical system S, in accordance with an embodiment of the present disclosure. FIG. 2A further shows ray-tracing through a CCR reflector. Three orthogonal reflecting planes are shown. An incident light ray is expressed by a unit vector in three Cartesian coordinates as follows:

$$n_i=(n_{ix},n_{iy},n_{iz}), \qquad (3)$$

wherein $|n_i|$=1, and wherein each plane reflection changes the sign of one of the coordinate components. The spherical coordinates $\varphi_{in}$ (azimuth) and $\theta_{in}$ (elevation) are shown, thereby facilitating the ray-tracing process.

Referring to FIG. 2B, this diagram illustrates a perspective view of a retroreflective optical system S, comprising a glass CCR, by example only, with a representation of direction and orientation of both incoming light 10 and outgoing light 20, in accordance with an embodiment of the present disclosure. The retroreflective optical system S, for creating a passive optical tag in an absence of electrical power, generally comprises: a retroreflector 100 comprising a surface 30 and a retroreflective element 50 disposed in relation to the surface 30, e.g., on an outer surface, the retroreflective element 50 configured to: passively impart a unique signature in relation to incoming light 10 by using at least one of spectral filtration and color filtration, whereby a plasmonic response is effectible; and reflect outgoing light 20 having the unique signature; and an optical device 70, e.g., comprising a CCR, having an input aperture 71 (FIG. 3), the optical device 70 disposed at a distance d from the retroreflector 100, and the optical device 70 configured to transmit the incoming light 10 and the outgoing light 20.

Still referring to FIG. 2B, in the system S, the optical device 70 is configured to: transmit the incoming light 10 originating from an optical source 80 (FIG. 3); and transmit the outgoing light 20 to the optical source 80. The retroreflective element 50 comprises at least one of: at least one thin metal film, at least one dielectric coating deposition, and at least one dielectric film deposition. The retroflector 100 comprises at least one of a concave configuration and a conical configuration. The retroflector 100 further comprises a grating (not shown) configured to selectively reflect the outgoing light 20 as a function of wavelength $\lambda$. The retroreflector 100 operates independently of orientation; and the retroreflector 100 is configured to reflect the outgoing light 20 having the unique signature, at a same angle as that of the incoming light 10.

Still referring to FIG. 2B, in the system S, the retroreflector 100 comprises a large field of view (FoV) in a range of approximately –85 degrees to approximately 85 degrees. In addition, the retroreflector 100 is insensitive to platform jitter. The retroreflector 100 is further configured to operate with the optical source 80; and the optical source 80 comprises a laser light source 81, a laser light detector 82, and a laser light signal processor 83 (FIG. 3). The retroreflector 100 is further configured to: receive the incoming light 10 comprising broadband incident light, and reflect the outgoing light 20, having the unique signature, comprising spectrally filtered light.

Still referring to FIG. 2B and referring back to FIG. 2A, if the azimuth and elevation angles are known, the unit vector rays are computable and expressed as follows:

$$n_i=(\sin\theta_{in}\cos\varphi_{in}, \sin\theta_{in}\sin\varphi_{in}, \cos\theta_{in}). \qquad (4)$$

As described herein, the angle of incidence upon a surface is critical to the excitation of surface waves. Thus, the ray's angle of incidence upon each of the three interior CCR surfaces is computable. The x-y plane (bottom) is designated as "A" which interacts with the first ray 21, e.g., of incoming light 10. The x-z plane (side) is designated as "B" which interacts with the second ray 22. The y-z plane (rear) is designated as "C" which interacts with a third ray 23. The fourth (final) ray 24 is reflected back in the direction from which the first ray 21 originated. The incidence angle of an incoming ray upon a surface is defined as the inverse cosine of the ray's unit vector component normal to such surface. For example, the surface A is in the x-y plane. Thus, the incidence angle of the first ray upon the surface A is $\cos^{-1}(n_{iz})$. Presented together, $$(\theta_A,\theta_B,\theta_C)=(\cos^{-1} n_{iz}, \cos^{-1} n_{iy}, \cos^{-1} n_{ix}). \qquad (5)$$

Still referring to FIG. 2B, within the CCR, the three incidence angles are now defined and are usable in surface wave reflectivity calculations. However, one ray tracing issue remains: the incident or incidence ray will refract at the CCR's flat entrance face. Therefore, a three-dimensional vector calculation is performed for tracing the incoming ray as it enters the CCR. The vector form of the equation, corresponding to Snell's refraction law, is as follows:

$$s_2 = \frac{N_1}{N_2}[U\times(-U\times s_1)] - U\sqrt{1-\left(\frac{N_1}{N_2}\right)^2(U\times s_1)\cdot(U\times s_1)}, \qquad (6)$$

wherein $s_2$=the refracted ray vector within the CCR, $s_1$=the incident ray vector upon the CCR, U=the unit normal vector corresponding to the CCR face, $N_1$=the refractive index of the medium outside the CCR face, e.g., air with $N_1$=1, and $N_2$=the refractive index of the solid CCR.

Referring to FIG. 3, this diagram illustrates a side view of, a retroreflective optical system S as implemented with an optical source 80, e.g., a laser light source, as an electro-optical arrangement, in accordance with an embodiment of the present disclosure. The system S, in this embodiment, comprises: a retroreflector 100 comprising a surface 30 (FIG. 2B) and a retroreflective element 50 disposed in relation to the surface 30, e.g., an outer surface, the retroreflective element 50 configured to: passively impart a unique signature in relation to incoming light 10 by using at least one of spectral filtration and color filtration, whereby a plasmonic response is effectible; and reflect outgoing light 20 having the unique signature; and an optical device 70 having an input aperture 71, the optical device 70, e.g., comprising a CCR, disposed at a distance d from the retroreflector 100, and the optical device 70 configured to transmit the incoming light 10 and the outgoing light 20.

Still referring to FIG. 3, in the system S, the optical device 70 is configured to: transmit the incoming light 10 originating from an optical source 80; and transmit the outgoing light 20 to the optical source 80. The retroreflective element 50 comprises at least one of: at least one thin metal film, at least one dielectric coating deposition, and at least one dielectric film deposition. The retroflector 100 comprises at least one of a concave configuration and a conical configuration. The retroflector 100 further comprises a grating (not shown) configured to selectively reflect the outgoing light 20 as a function of wavelength λ. The retroreflector 100 operates independently of orientation; and the retroreflector 100 is configured to reflect the outgoing light 20 having the unique signature, at a same angle as that of the incoming light 10.

Still referring to FIG. 3, the retroreflective element 50 comprises a retroreflective coating, such as at least one of a metal coating and a metal film, in accordance with some embodiments of the present disclosure. Purity and thickness of the retroreflective coating is controllable and encompassed by the present disclosure. For disposing the retroreflective element 50 on the surface 30, at least one technique is used, such as at least one of electron-beam evaporation, thermal evaporation, sputtering, molecular beam epitaxy (MBE), and the like. The retroreflective element 50 further comprises at least one of: at least one adhesive layer disposed between the retroreflector 100 and the retroreflective coating and at least one protective layer disposed on the retroreflective coating, wherein at least one of: the at least one adhesive layer and the at least one protective layer are customizable in relation to a particular implementation or desired configuration.

Still referring to FIG. 3, the retroreflective coating may further, or alternatively, comprises a non-metal coating, such as a dielectric polar crystal layer, wherein purity and thickness of the retroreflective coating is also controllable, in accordance with other embodiments of the present disclosure. Depositing a non-metal coating on a solid retroreflector would be challenging in some circumstances. For example, a non-metal coating comprises silicon carbide (SiC) layer, wherein the SiC layer is formable by a technique, such as growth thereof on a flat silicon (Si) substrate, e.g., in a furnace with carbon-containing gas flowing over the Si substrate. Noted is that SiC has a tendency to on certain crystal planes. Thus, SiC and other crystals may not readily grow on all outer surfaces of the retroreflector 100, e.g., all three back sides of an example retroreflector. However, since the non-metal coating comprises many possible retroreflector materials and many possible dielectric films, its formation process is customizable for each particular combination of retroreflective coatings. By example only, the SiC is independently growable on an expendable material, e.g., as a thin SiC film, and subsequently decoupled therefrom for recoupling to the surface 30, wherein the thin SiC film is adherable to the Si retroreflector 100 as needed for any given implementation. Further, dielectric layers are also growable by MBE, and the like.

Still referring to FIG. 3, the retroreflector 100 comprises a solid configuration, in accordance with embodiments of the present disclosure. The retroreflector 100 comprises at least one material of, such as for customizing operability in any wavelength band, e.g., a UV-spectrum-transparent material, a visible-spectrum-transparent material, a near-IR-spectrum-transparent material, a mid-IR-spectrum-transparent material, and a far-IR-spectrum-transparent material. For example, for operating in a UV band, the UV-spectrum-transparent material comprises a UV-spectrum-transparent fused silica/quartz material. For operating in a visible band, the visible-spectrum-transparent material comprises BK7 glass layer. For operating in a near-IR band, the near-IR-spectrum-transparent material comprises Si. For mid-IR band, mid-IR-spectrum-transparent material comprises at least one of Si, germanium (Ge), and the like. The solid configuration of the retroreflector 100 comprises a corner cube, by example only, configured to reflect light back to the source, even in the absence of thin films for generating plasmonics resonance.

Still referring to FIG. 3, distinct from mere related art mirrored coatings, the retroreflective coating of the present disclosure is wavelength-selective coating and is thereby customizable for a plurality of implementations. By example only, the system S is operable by light entering the retroreflector 100, e.g., through the optical device 70, whereby light is internally reflected by an angled surface, rather than by related art parallel surfaces, e.g., an entrance surface and a parallel rear reflection surface. By way of at least internally reflecting light via the angled surface, the system S of the present disclosure is configured to at least one of: generate surface plasmon polaritons (metal films) and generate surface phonon polaritons (polar crystals). Related art related art parallel surfaces are not configured to generate such polaritons. Distinct from a related art "mirror," e.g., having a thick aluminum coating to ensure total reflection for all colors and a protective paint disposed on the thick aluminum coating to prevent scratching and peeling thereof, the retroreflective coating of the present disclosure, comprising a very thin metal layer, such as silver (Ag), e.g., having a thickness of approximately 0.5 micrometers, ensures partial, conditional reflection for achieving selective reflection. In the retroreflective coating of the present disclosure, most colors would reflect; however, when the surface wave conditions are met, such as at special angles and wavelengths, light energy couples "through" the retroreflective coating, being thin, leaky, and having a thickness of approximately 0.5 micron, and into these light waves, wherein optical power is then lost, and wherein a distinct signature is generated.

Still referring to FIG. 3, in some embodiments of the present disclosure, the retroreflective coating comprises a polar crystal material, wherein the polar crystal material comprises a crystalline structure and is not amorphous, e.g., the polar crystal material comprises a lattice structure on the atomic scale. Accordingly, in some embodiments, the retroreflective coating comprises polar crystal material, wherein the polar crystal material comprises at least one of: a fully-crystalline film structure, a micro-crystalline film structure, and a nano-crystalline film structure. In some embodiments of the present disclosure, the retroreflective coating comprises smooth layering, e.g., a "silver on quartz" layer operating as a visible-band device, wherein the "silver on quartz" layer comprises a thickness in a range of approximately 35 nm to approximately 65 nm, and preferably 50 nm, of silver layer over quartz having an area of approximately 5 mm×approximately 5 mm area.

Still referring to FIG. 3, in the system S, the retroreflector 100 comprises a large field of view (FoV) in a range of approximately −85 degrees to approximately 85 degrees. In addition, the retroreflector 100 is insensitive to platform jitter. The retroreflector 100 is further configured to operate with the optical source 80; and the optical source 80 comprises a laser light source 81, a laser light detector 82, and a laser light signal processor 83. The retroreflector 100 is further configured to: receive the incoming light 10 comprising broadband incident light, and reflect the outgoing light 20, having the unique signature, comprising spectrally filtered light.

Figure 4:
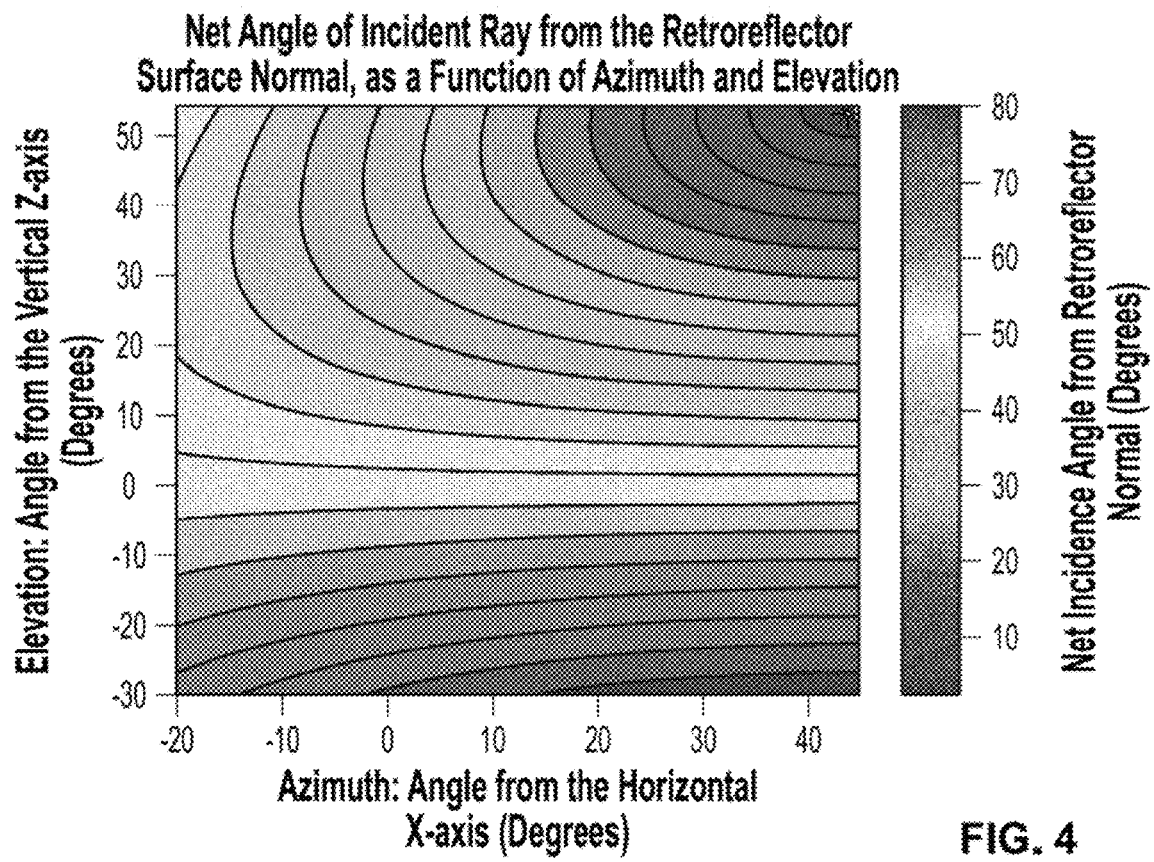
FIG. 4 is a graph illustrating a net angle of an incident light ray as measured from a retroreflector normal surface, wherein both an elevation (angle from a vertical z-axis) in degrees and a net incidence (angle from a retroreflector normal surface) in degrees are shown as a function of azimuth (an angle from a horizontal x-axis) in degrees, in accordance with an embodiment of the present disclosure.

Referring to FIG. 4, this graph illustrates a net angle of an incident light ray as measure from a retroreflector normal surface, wherein both an elevation (angle from a vertical z-axis) in degrees and a net incidence (angle from a retroreflector normal surface) in degrees are shown as a function of azimuth (an angle from a horizontal x-axis) in degrees, in accordance with an embodiment of the present disclosure. Configuring a CCR is visualizable by taking a perfect cube and "cutting-off" one corner, wherein the lengths of the x-axis, the y-axis, and the z-axis are equal. Such axial symmetry constrains the unit vector normal to the surface as comprising three equal values. Thus, the CCR's unit vector surface normal is expressed as follows:

$$U = \left(\frac{1}{\sqrt{3}}, \frac{1}{\sqrt{3}}, \frac{1}{\sqrt{3}}\right), \quad (7)$$

which, as per Eq. 4, corresponds to an azimuth angle of $\varphi_u=45°$ and an elevation angle of $\theta=54.7°$. Any ray that is incident at these angles is not refracted. For further understanding of the range of azimuth and elevation angles that are reasonably accessible to the CCR, FIG. 4 shows an idealized net total angle, e.g., a FoV half-angle, of the incident ray from the CCR surface normal as a color mapping. The incident ray azimuth angle of $\varphi_u=45°$ and the elevation angle of $\theta=54.7°$ yield a net angle of 0°. Modestly negative values, e.g., down to approximately 30°, of azimuth and elevation are possible and yield effective CCR incident angles of approximately 60° and approximately 80°.

Figure 5:
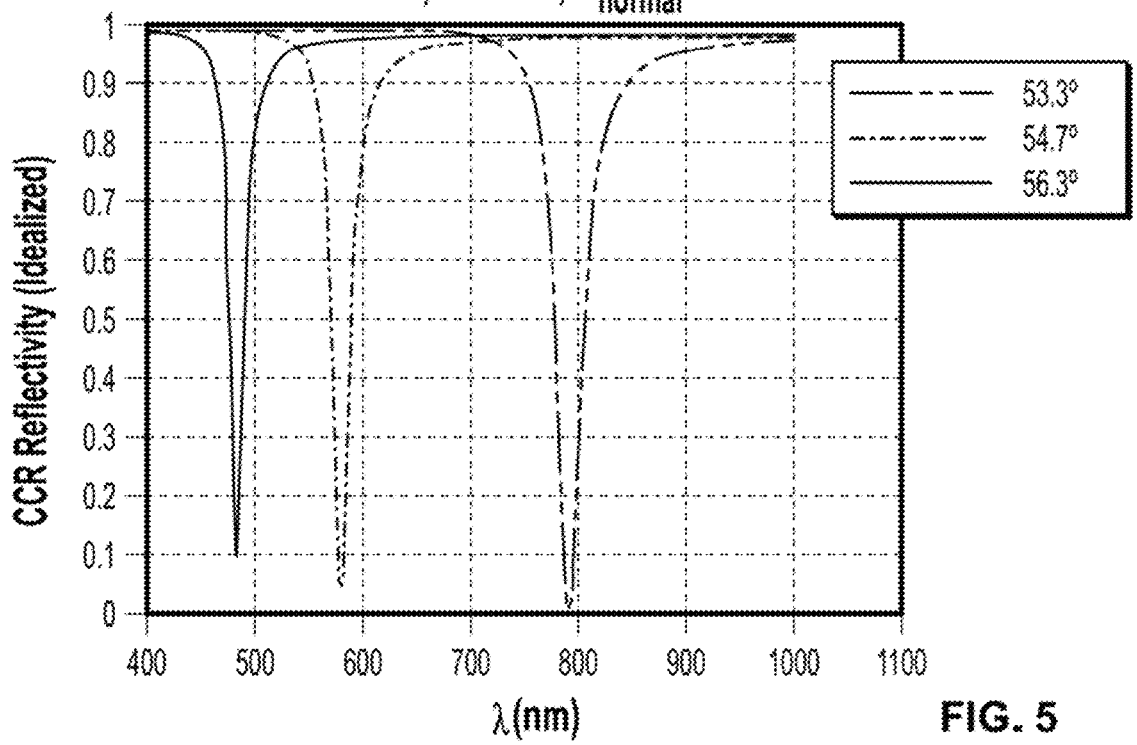
FIG. 5 is a graph illustrating an idealized corner cube retroreflector (CCR) reflectivity (light) ray trace, showing three reflection minima, in accordance with an embodiment of the present disclosure.

Referring to FIG. 5, this graph illustrates an idealized CCR reflectivity (light) ray trace, showing three reflection minima, in accordance with an embodiment of the present disclosure. With an understanding of light rays that are incident upon the CCR and of refraction at the CCR face, the reflectance at the inner surface that support SPPs is calculated. Surface wave reflectance is solvable by using numerical calculations, e.g., using MATLAB® software, whereby Maxwell's equations are solvable in one dimension (longitudinal propagation) for s-polarization and p-polarization. FIG. 5 shows an idealized case, using purely p-polarized broadband illumination, a glass CCR with a refractive index of 1.4, a 55-nanometer (nm) gold film deposited on each of the three reflection faces, a thick layer of protective dielectric film coating having an index of 1.1 that of the gold's index, an azimuth incident angle of 42°, and an elevation incident angle of 54.7°, a net incidence ray angle of 2.4° from the CCR face and three distinct reflection minima, corresponding to SPP excitation at least of the three faces are observed. Realistically, having a pure p-polarization incident upon all three faces within the CCR is not possible; however, employing unpolarized light is possible. Also, light is reflected from one cube face to another cube face, whereby the resulting single spectrum comprises three unpolarized spectra multiplied together.

Figure 6A:
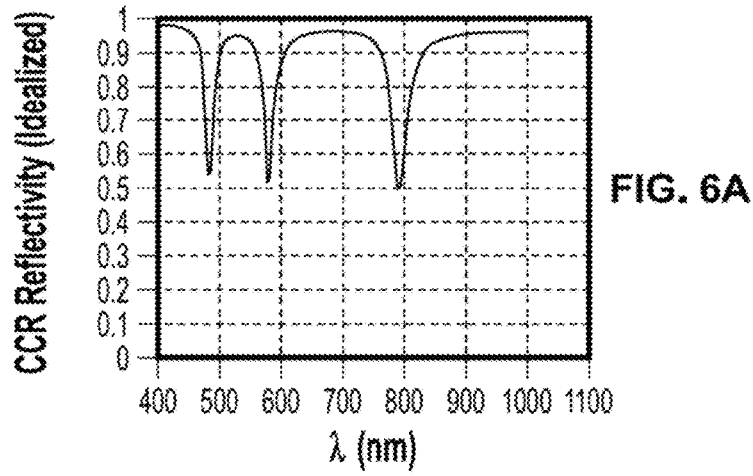
FIG. 6A is a graph illustrating an idealized CCR reflectivity as a function of wavelength for a retroreflective element comprising gold (Au), with an unpolarized spectrum (averaged s-polarization and p-polarization) after three-face multiplication corresponding to a first parameter set, in accordance with an embodiment of the present disclosure.

Referring to FIG. 6A, this graph illustrates an idealized CCR reflectivity as a function of wavelength λ (nm) for a retroreflective element comprising Au, with an unpolarized spectrum (averaged s-polarization and p-polarization) after three-face multiplication corresponding to a first parameter set, as shown in FIG. 5, in accordance with an embodiment of the present disclosure. The unpolarized spectrum corresponds to the first set of parameters, as shown in FIG. 5.

Figure 6B:
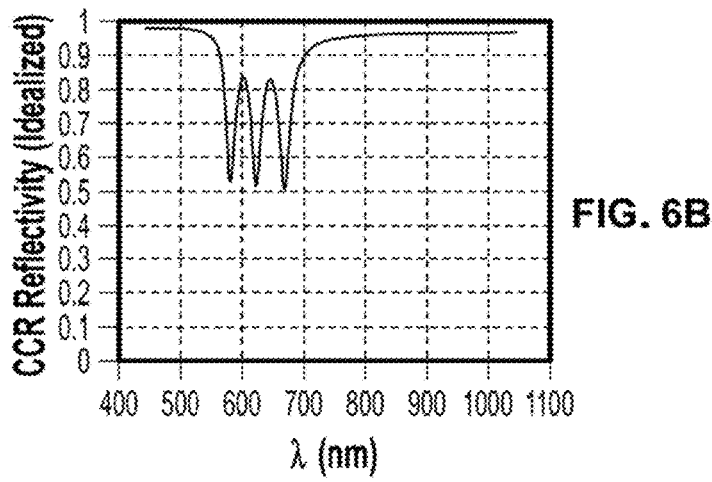
FIG. 6B is a graph illustrating an idealized CCR reflectivity as a function of wavelength for a retroreflective element comprising Au, with an unpolarized spectrum (averaged s-polarization and p-polarization) after three-face multiplication, corresponding to a second parameter set, in accordance with an embodiment of the present disclosure.

Referring to FIG. 6B, this graph illustrates an idealized CCR reflectivity as a function of wavelength λ (nm) for a retroreflective element comprising Au, with an unpolarized spectrum (averaged s-polarization and p-polarization) after three-face multiplication, corresponding to a second parameter set, as shown in FIG. 5, in accordance with an embodiment of the present disclosure.

Figure 6C:
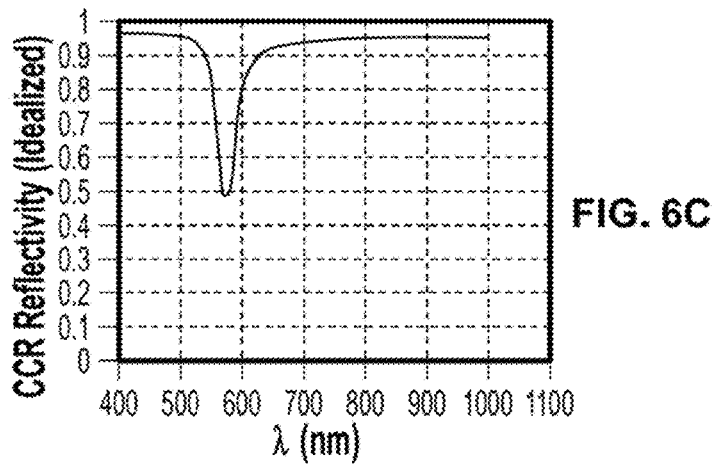
FIG. 6C is a graph illustrating an idealized CCR reflectivity as a function of wavelength for a retroreflective element comprising Au, with an unpolarized spectrum (averaged s-polarization and p-polarization) after three-face multiplication, corresponding to a third parameter set, in accordance with an embodiment of the present disclosure.

Referring to FIG. 6C, this graph illustrates an idealized CCR reflectivity as a function of wavelength λ (nm) for a retroreflective element comprising Au, with an unpolarized spectrum (averaged s-polarization and p-polarization) after three-face multiplication, corresponding to a third parameter set, as shown in FIG. 5, in accordance with an embodiment of the present disclosure. The ray is incident normal to the CCR, whereby all reflections are symmetric and all three spectral minima are co-located.

Referring back to FIGS. 6A-6C, the gold-coated CCR's reflectivity spectrum is highly sensitive to incidence azimuth and elevation angles. Dramatic wavelength shifts occur with minute rotations, thereby spreading from a single minimum at 580 nm when illuminated 0° from the face normal to three minima spanning from 480 nm to 790 nm when illuminated off-axis by only 2.4°. The examples demonstrate the manner in which the retroreflective optical system of the present disclosure may be configured for spectroscopic tagging, identification, and orientation analysis. Many additional materials and parameter may also be used for visible-band and near-IR-band implementations. Variable parameters include, but are not limited to, the corner cube material and, thus, the CCR refractive index, the type and thickness of plasmonic metal film being deposited on the three CCR reflecting surfaces, the ability for selecting or forgoing a protective dielectric overcoat on the metal film, and selecting the input polarization, such as linear polarization, elliptical polarization, and no polarization.

Still referring back to FIGS. 6A-6C, while the visible spectrum may have many applications, the mid-IR and far-IR ranges in the electromagnetic spectrum provide the system and methods of the present disclosure with features for implementations, such as military thermal imaging, biochemical sensing, and surface phonon-polariton excitation in the absence of metals. A polar crystalline material, e.g., SiC, comprises a permittivity in a range of less than zero in the IR band (FIG. 1B) and provides a surface wave response that is similar to that evoked by gold, silver, and other noble metals. Metal-free devices, as usable in the system and methods of the present disclosure, are operable in higher-temperature environments, such as in a temperature of approximately −320 degrees F., e.g., the temperature of liquid nitrogen, up to, and including, approximately the melting point of a given material, and in settings where a more robust material is required. Since SiC comprises a hardness in a range that approximates that of diamond, SiC is useful for implementations where noble metals may be unduly malleable.

Figure 7A:
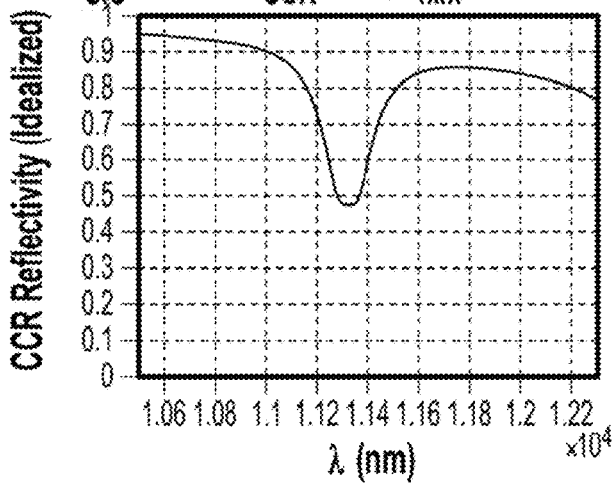
FIG. 7A is a graph illustrating an idealized CCR reflectivity as a function of wavelength for a retroreflective element comprising silicon carbide (SiC), with an unpolarized spectrum (averaged s-polarization and p-polarization) after three-face multiplication, corresponding to a first parameter set, in accordance with an embodiment of the present disclosure.
Figure 7B:
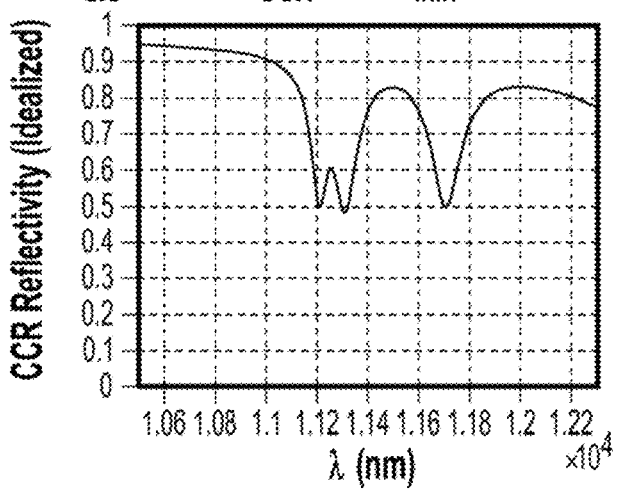
FIG. 7B is a graph illustrating an idealized CCR reflectivity as a function of wavelength for a retroreflective element comprising SiC, with an unpolarized spectrum (averaged s-polarization and p-polarization) after three-face multiplication, corresponding to a second parameter set, in accordance with an embodiment of the present disclosure.
Figure 7C:
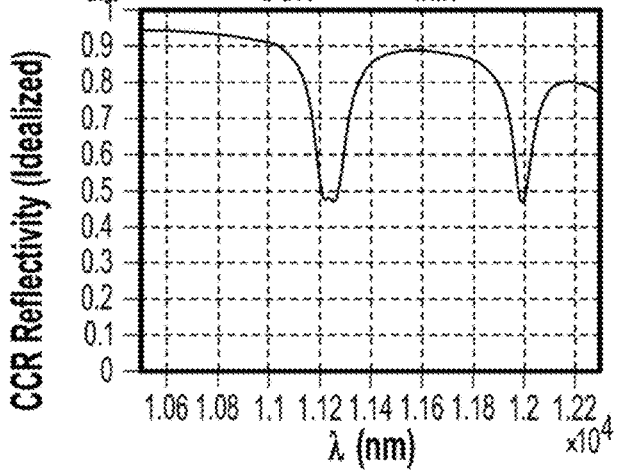
FIG. 7C is a graph illustrating an idealized CCR reflectivity as a function of wavelength for a retroreflective element comprising SiC, with an unpolarized spectrum (averaged s-polarization and p-polarization) after three-face multiplication, corresponding to a third parameter set, in accordance with an embodiment of the present disclosure.

Referring to FIGS. 7A-7C, together, the system and methods of the present disclosure utilize SiC as an SPP-supporting material with a thickness in a range of approximately 10.6 microns to approximately 12.3 microns (μm). Calculations are performed by using the following parameters: a 750-nm SiC layer is deposited on each corner cube face, wherein the CCR comprises silicon (Si) with a refractive index of 3.48 and the thick dielectric overcoat comprises a refractive index of 2. Unlike the visible-spectrum gold and glass CCR arrangement, displaying a higher angle sensitivity and narrow angular range, the IR-spectrum SiC and Si CCR combination displays extraordinary range, e.g., from normal incidence to at least 800, by using the high-index Si prism, thereby strongly refracting incident rays toward the central axis and consequently limiting the range of internal angles incident upon the three reflecting surfaces.

Referring to FIG. 7A, this graph illustrates an idealized CCR reflectivity as a function of wavelength λ (nm) for a retroreflective element comprising SiC, with an unpolarized spectrum (averaged s-polarization and p-polarization) after three-face multiplication, corresponding to a first parameter set, in accordance with an embodiment of the present disclosure. The spectrum shown is resolved for a net incident angle of 0°.

Referring to FIG. 7B, this graph illustrates an idealized CCR reflectivity as a function of wavelength λ (nm) for a retroreflective element comprising SiC, with an unpolarized spectrum (averaged s-polarization and p-polarization) after three-face multiplication, corresponding to a second parameter set, in accordance with an embodiment of the present disclosure. The spectrum shown is resolved for a net incident angle of 66.8°.

Referring to FIG. 7C, this graph illustrates an idealized CCR reflectivity as a function of wavelength λ (nm) for a retroreflective element comprising SiC, with an unpolarized spectrum (averaged s-polarization and p-polarization) after three-face multiplication, corresponding to a third parameter set, in accordance with an embodiment of the present disclosure. The spectrum shown is resolved for a net incident angle of 82.5°.

Referring to FIG. 8, this flow diagram illustrates a method M1 of fabricating a retroreflective optical system S for creating a passive optical tag in an absence of electrical power, in accordance with an embodiment of the present disclosure. The method M1 comprises: providing a retroreflector 100, as indicated by block 801, providing the retroreflector 100 comprising providing a surface 30 and providing a retroreflective element 50 disposed in relation to the surface 30, e.g., an outer surface, providing the retroreflective element 50 comprising configuring the retroreflective element 50 to: passively impart a unique signature in relation to incoming light 10 by using at least one of spectral filtration and color filtration, whereby a plasmonic response is effectible; and reflect outgoing light 20 having the unique signature; and providing an optical device 70, as indicated by block 802, providing the optical device 70 comprising providing an input aperture 71, providing the optical device 70 comprising disposing the optical device 70 at a distance d from the retroreflector 100 and configuring the optical device 70 to transmit the incoming light 10 and the outgoing light 20.

Still referring to FIG. 8, in the method M1, providing the optical device 70 comprises configuring the optical device 70 to: transmit the incoming light 10 originating from an optical source 80; and transmit the outgoing light 20 to the optical source 80. Providing the retroreflective element 50 comprises providing at least one of: at least one thin metal film, at least one dielectric coating deposition, and at least one dielectric film deposition. Providing the retroflector 100 comprises providing at least one of: a concave configuration and a conical configuration; and providing the retroflector 100 further comprises providing a grating (not shown) configured to selectively reflect the outgoing light 20 as a function of wavelength. Providing the retroreflector 100 comprises providing the retroreflector 100 as operable independently of orientation; and providing the retroreflector 100 comprises configuring the retroreflector 100 to reflect the outgoing light 20, having the unique signature, at a same angle as that of the incoming light 10. Providing the retroflector 100 comprises providing a solid configuration, providing the solid configuration comprising providing a corner cube configuration. Providing the retroreflector 100 comprises providing a material selected from a group consisting essentially of a UV-spectrum-transparent material, a visible-spectrum-transparent material, a near-IR-spectrum-transparent material, a mid-IR-spectrum-transparent material, and a far-IR-spectrum-transparent material.

Still referring to FIG. 8, providing the retroreflector 100 comprises a large FoV in a range of approximately −85 degrees to approximately 85 degrees. Providing the retroreflector 100 comprises providing the retroreflector 100 as insensitive to platform jitter. Providing the retroreflector 100 further comprises configuring the retroreflector 100 to operate with the optical source 80; and providing the optical source 80 comprises: providing a laser light source 81, providing a laser light detector 82, and providing a laser light signal processor 83. Providing the retroreflector 100 further comprises configuring the retroreflector 100 to: receive the incoming light 10 comprising broadband incident light, and reflect the outgoing light 20, having the unique signature, comprising spectrally filtered light.

Figure 9:
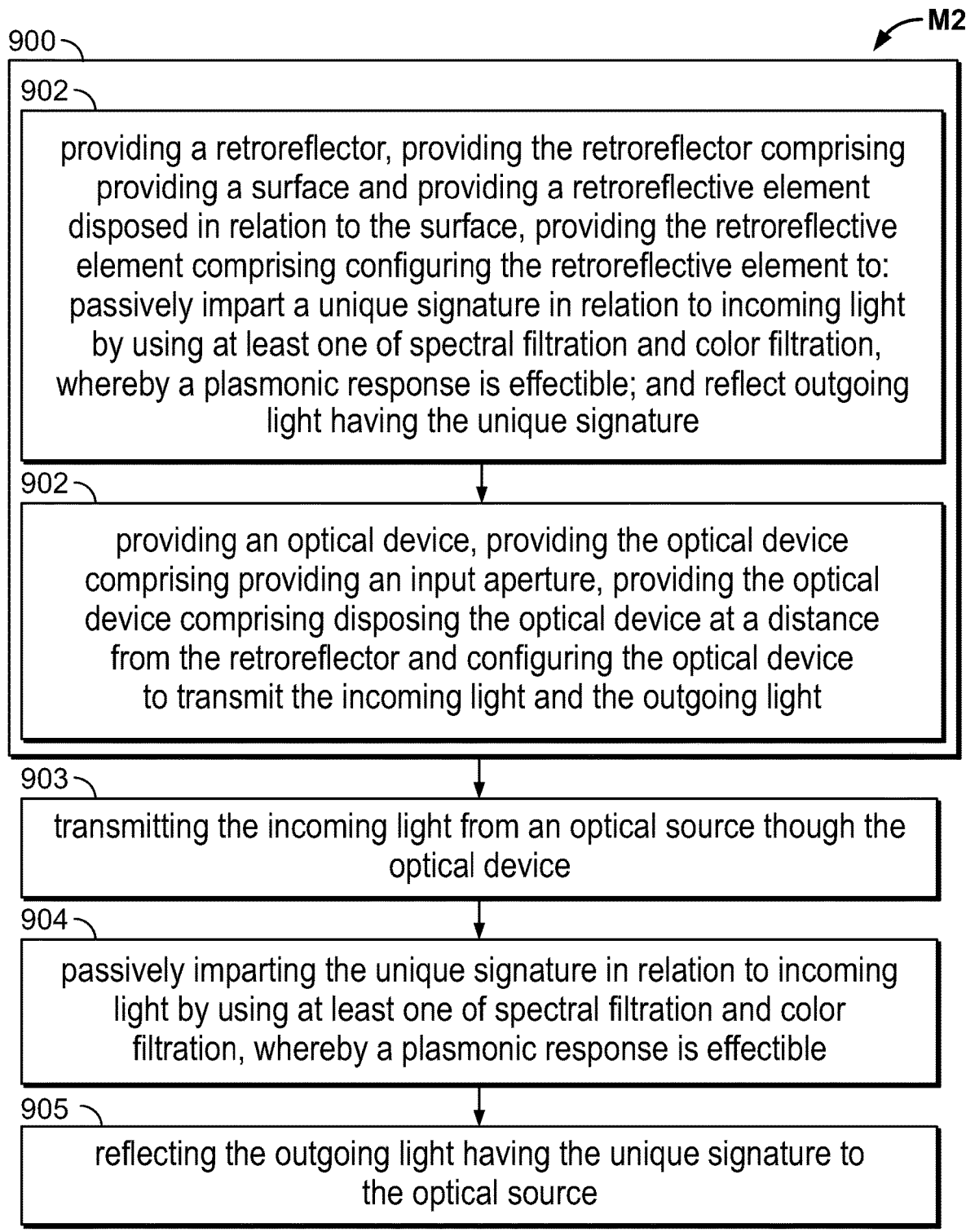
FIG. 9 is a flow diagram illustrating a method of creating a passive optical tag in an absence of electrical power by way of a retroreflective optical system, in accordance with an embodiment of the present disclosure.

Referring to FIG. 9, this flow diagram illustrates a method M2 of creating a passive optical tag in an absence of electrical power by way of a retroreflective optical system S, in accordance with an embodiment of the present disclosure. The method M2 comprises: providing the retroreflective optical system S, as indicated by block 900, providing the retroreflective optical system S comprising: providing a retroreflector 100, as indicated by bock 901, providing the retroreflector 100 comprising providing a surface 30 and providing a retroreflective element 50 disposed in relation to the surface 30, providing the retroreflective element 50 comprising configuring the retroreflective element 50 to: passively impart a unique signature in relation to incoming light 10 by using at least one of spectral filtration and color filtration, whereby a plasmonic response is effectible; and reflect outgoing light 20 having the unique signature; and providing an optical device 70, as indicated by block 902, providing the optical device 70 comprising providing an input aperture 71, providing the optical device 70 comprising disposing the optical device 70 at a distance d from the retroreflector 100 and configuring the optical device 70 to transmit the incoming light 10 and the outgoing light 20; transmitting the incoming light 10 from an optical source 80 though the optical device 70, as indicated by block 903; passively imparting the unique signature in relation to incoming light 10 by using at least one of spectral filtration and color filtration, whereby a plasmonic response is effectible, as indicated by block 904; and reflecting the outgoing light 20 having the unique signature to the optical source 80, as indicated by block 905. Providing the retroreflector 100, as indicated by bock 901, comprises providing at least one of: at least one thin metal film, at least one dielectric coating deposition, and at least one dielectric film deposition. Providing the retroflector 100 comprises providing a solid configuration, providing the solid configuration comprising providing a corner cube configuration. Providing the retroreflector 100 comprises providing a material selected from a group consisting essentially of a UV-spectrum-transparent material, a visible-spectrum-transparent material, a near-IR-spectrum-transparent material, a mid-IR-spectrum-transparent material, and a far-IR-spectrum-transparent material.

It is understood that many additional changes in the details, materials, steps, and arrangement of parts, which have been herein described and illustrated to explain the nature of the invention, may be made by those skilled in the art within the principle and scope of the invention as expressed in the appended claims.

What is claimed:

1. A passive optical tag, comprising:
a retroreflector for receiving incoming light and for transmitting outgoing light, the retroreflector retroreflecting the incoming light as the outgoing light via a respective reflection at each of at least one surface of the retroreflector; and
a plasmonic thin film of uniform thickness disposed on each of the at least one surface of the retroreflector, the plasmonic thin film having negative permittivity producing a plasmonic response that spectrally filters the incoming light during the respective reflection at each of the at least one surface for imparting a spectral signature upon the outgoing light, the spectral signature uniquely distinguishing the passive optical tag among a plurality of similar optical tags, which include the passive optical tag but impart different spectral signatures.

2. The passive optical tag of claim 1, wherein the plasmonic thin film comprises at least one of: at least one thin metal film and at least one dielectric film.

3. The passive optical tag of claim 1,
wherein the retroflector comprises a solid configuration, the solid configuration comprising a corner cube configuration, and
wherein the retroflector comprises a material selected from a group consisting essentially of a UV-spectrum-transparent material, a visible-spectrum-transparent material, a near-IR-spectrum-transparent material, a mid-IR-spectrum-transparent material, and a far-IR-spectrum-transparent material.

4. The passive optical tag of claim 1,
wherein the retroreflector operates independently of orientation, and
wherein the retroreflector is configured to transmit the outgoing light, having the unique spectral signature, at a same angle as that of the incoming light.

5. The passive optical tag of claim 1, wherein the retroreflector comprises a large field of view in a range of approximately −85 degrees to approximately 85 degrees.

6. The passive optical tag of claim 1, wherein the retroreflector is insensitive to platform jitter.

7. The passive optical tag of claim 1, wherein the retroreflector is configured to:
receive the incoming light comprising broadband incident light, and
transmit the outgoing light, having the unique spectral signature.

8. A method of fabricating a retroreflective optical system for remotely identifying a passive optical tag among a plurality of similar optical tags imparting different spectral signatures, comprising:
providing a retroreflector for receiving incoming light and for transmitting outgoing light, the retroreflector retroreflecting the incoming light as the outgoing light via a respective reflection at each of at least one surface of the retroreflector;
providing a plasmonic thin film of uniform thickness disposed on each of the at least one surface of the retroreflector, the plasmonic thin film having negative permittivity producing a plasmonic response that spectrally filters the incoming light during the respective reflection at each of the at least one surface for imparting a spectral signature upon the outgoing light, the spectral signature uniquely distinguishing the passive optical tag among the similar optical tags, which include the passive optical tag but impart the different spectral signatures; and
providing an optical device disposed at a distance from the retroreflector and configured to receive the outgoing light transmitted from the retroreflector of the passive optical tag and to remotely identify the passive optical tag from the unique spectral signature of the outgoing light received at the optical device.

9. The method of claim 8, wherein providing the plasmonic thin film comprises providing at least one of: at least one thin metal film and at least one dielectric film.

10. The method of claim 8,
wherein providing the retroflector comprises providing a solid configuration, providing the solid configuration comprising providing a corner cube configuration, and
wherein providing the retroreflector comprises providing a material selected from a group consisting essentially of a UV-spectrum-transparent material, a visible-spectrum-transparent material, a near-IR-spectrum-transparent material, a mid-IR-spectrum-transparent material, and a far-IR-spectrum-transparent material.

11. The method of claim 8,
wherein providing the retroreflector comprises providing the retroreflector as operable independently of orientation, and
wherein providing the retroreflector comprises configuring the retroreflector to transmit the outgoing light, having the unique spectral signature, at a same angle as that of the incoming light.

12. The method of claim 8, wherein providing the retroreflector comprises a large field of view in a range of approximately −85 degrees to approximately 85 degrees.

13. The method of claim 8, wherein providing the retroreflector comprises providing the retroflector as insensitive to platform jitter.

14. The method of claim 8, wherein providing the retroreflector comprises configuring the retroreflector to:
receive the incoming light comprising broadband incident light, and
transmit the outgoing light, having the unique spectral signature.

15. The passive optical tag of claim 1, wherein:
the uniform thickness of the plasmonic thin film is sufficiently thin so that an evanescent electric field extends through the plasmonic thin film and for at least one specific wavelength excites the plasmonic response at an outer interface of the plasmonic thin film; and
the plasmonic response attenuates internal reflection for the at least one specific wavelength during the respective reflection at each of the at least one surface of the retroreflector, such that the outgoing light has the unique spectral signature, which includes attenuating the at least one specific wavelength from the incoming light.

16. The passive optical tag of claim 15, wherein:
the different spectral signatures of the similar optical tags uniquely distinguish the similar optical tags from one another because parameters are selected to impart the different spectral signatures; and the parameters include a refractive index of a material of the retroreflector, a material and purity of the plasmonic thin film, the uniform thickness of the plasmonic thin film, whether the outer interface of the plasmonic thin film has a protective dielectric overcoat or forgoes the protective dielectric overcoat, and a positive permittivity of a material of the protective dielectric overcoat.

17. The passive optical tag of claim 1, wherein:

the retroreflector is a solid corner cube retroreflector with the at least one surface being three reflective surfaces of the solid corner cube retroreflector;

the uniform thickness of the plasmonic thin film disposed on each of the three reflective surfaces is sufficiently thin so that an evanescent electric field extends through the plasmonic thin film and, for at least one specific wavelength at each orientation of incident angles, excites the plasmonic response at an outer interface of the plasmonic thin film; and the plasmonic response attenuates internal reflection for the at least one specific wavelength at each orientation of the incident angles during the respective reflection at each of the three reflective surfaces, such that the outgoing light has the unique spectral signature, which includes from the incoming light attenuating the at least one specific wavelength for the orientation of the incident angles.

18. The passive optical tag of claim 17, wherein the unique spectral signature of the passive optical tag not only uniquely distinguishes the passive optical tag among the similar optical tags, but also identifies the orientation of the passive optical tag relative to the incident angles of the incoming and outgoing light.

19. The passive optical tag of claim 1, wherein the plasmonic thin film is a polar crystal of SiC having the negative permittivity in the infrared and producing the plasmonic response from surface phonon polaritons at an outer interface of the plasmonic thin film for spectrally filtering the incoming light to impart the unique spectral signature in the infrared of the outgoing light.

20. A system for remotely identifying the passive optical tag of claim 1 among the plurality of similar optical tags, comprising:

the plurality of similar optical tags including the passive optical tag, each of the similar optical tags imparting a respective one of the different spectral signatures;

an optical detector for remotely receiving the outgoing light transmitted from the retroreflective element of the passive optical tag; and a signal processor for matching the unique spectral signature of the outgoing light received at the optical detector with a specific spectral signature of the different spectral signatures, and for remotely identifying the passive optical tag among the similar optical tags from the specific spectral signature matching the unique spectral signature of the passive optical tag.

* * * * *